(12) United States Patent
Wilk et al.

(10) Patent No.: US 7,345,032 B2
(45) Date of Patent: Mar. 18, 2008

(54) METHODS FOR THE PREPARATION OF {2-[(8,9)-DIOXO-2,6-DIAZA-BICYCLO[5.2.0]-NON-1(7)-EN-2-YL]ETHYL}PHOSPHONIC ACID AND ESTERS THEREOF

(75) Inventors: Bogdan K. Wilk, New City, NY (US); Galina Vid, New City, NY (US); Weiguo Liu, Parsippany, NJ (US); Xinxu Shi, Flushing, NY (US)

(73) Assignee: Wyeth, Madison, NJ (US)

( * ) Notice: Subject to any disclaimer, the term of this patent is extended or adjusted under 35 U.S.C. 154(b) by 115 days.

(21) Appl. No.: 10/969,715

(22) Filed: Oct. 20, 2004

(65) Prior Publication Data
US 2005/0090470 A1    Apr. 28, 2005

Related U.S. Application Data

(60) Provisional application No. 60/513,611, filed on Oct. 22, 2003.

(51) Int. Cl.
  *A61K 31/675* (2006.01)
  *C07D 223/00* (2006.01)
  *C07F 9/553* (2006.01)

(52) U.S. Cl. ........................ 514/80; 540/542

(58) Field of Classification Search ............. 514/80; 540/542
  See application file for complete search history.

(56) References Cited

U.S. PATENT DOCUMENTS

| | | | |
|---|---|---|---|
| 4,390,701 A | 6/1983 | Algieri et al. | 546/235 |
| 5,124,319 A | 6/1992 | Baudy et al. | 514/80 |
| 5,168,103 A | 12/1992 | Kinney et al. | 514/221 |
| 5,212,291 A | 5/1993 | Murdock et al. | 536/6.4 |
| 5,240,946 A | 8/1993 | Kinney et al. | 514/364 |
| 5,583,123 A | 12/1996 | Lombaert et al. | 514/92 |
| 5,593,659 A | 1/1997 | Winchell et al. | 424/9.363 |
| 5,595,983 A | 1/1997 | Watkins et al. | 514/85 |
| 5,602,115 A | 2/1997 | Nugent et al. | 514/105 |
| 5,708,152 A | 1/1998 | Lohmann et al. | 536/20 |
| 5,990,307 A | 11/1999 | Asselin et al. | 540/542 |
| 6,011,168 A | 1/2000 | Asselin et al. | 558/172 |
| 2003/0114444 A1 | 6/2003 | Brandt et al. | 514/221 |
| 2004/0082543 A1 | 4/2004 | Cheung | 514/80 |
| 2005/0004079 A1 | 1/2005 | Benjamin et al. | 514/80 |
| 2005/0004080 A1 | 1/2005 | Baudy et al. | 514/80 |
| 2005/0142192 A1 | 6/2005 | Benjamin et al. | 514/80 |
| 2006/0079679 A1 | 4/2006 | Benjamin et al. | 514/80 |

FOREIGN PATENT DOCUMENTS

| | | |
|---|---|---|
| DE | 1518660 | 8/1969 |
| EP | 0 496 561 A2 | 7/1992 |
| EP | 0 778 023 A1 | 6/1997 |
| EP | 994 107 A1 | 4/2000 |
| WO | WO 98/15542 | 4/1998 |
| WO | WO 99/06417 | 2/1999 |
| WO | WO 99/64041 A1 | 12/1999 |
| WO | WO 03/031416 A2 | 4/2003 |
| WO | WO 2004/039371 A2 | 5/2004 |
| WO | WO 2004/091633 A1 | 10/2004 |
| WO | WO 2004/092189 A1 | 10/2004 |

OTHER PUBLICATIONS

B. Engelsen, "Neurotransmitter glutamate: its clinical importance", Acta Neurol Scand. (1986) Nov.;74(5):337-55.
Boast, et al., "The N-methyl-D-aspartate antagonists CGS 19755 and CPP reduce ischemic brain damage in gerbils", Brain Research, 442 (1998) 345-348.
Schmutz, M. et al., *Abs. Soc. Neurosci.* 1988, 14, 864.
J.C.Watkins, "Excitatory Amino Acid Transmitters", Ann. Rev. Pharmacol. Toxicol. (1981) 21:165-204.
Turski, et al., "Protection of substantia nigra from MPP+ neurotoxicity by N-methyl-D-aspartate antagonists", (Jan. 31, 1991), Nature vol. 349:414-418.
Lehmann, et al., "CPP, a Selective N-Methyl-D-Aspartate (NMDA)-Type Receptor Antagonist: Characterization In Vitro and In Vivo", The Journal of Pharmacology and Experimental Therapeutics, vol. 240, No. 3:737-746, 1987.
Choi, "Calcium-mediated neurotoxicity: relationship to specific channel types and role in ischemic damage", Trends Neurosci. Oct. 1988;11(10):465-9.
Maragos et al., "Glutamate dysfunction in Alzheimer's disease; an hypothesis", TINS (Feb. 1987[10]):65-68.
Lehmann, et al. "CGS 19755, a selective and competitive N-methyl-D-aspartate-type excitatory amino acid receptor antagonist." J Pharmacol Exp Ther. Jul. 1988;246(1):65-75.
Johnson, et al., "Excitatory amino acid neurotransmission.", J Med Chem. Nov. 1988;31(11):2057-66.
Morita, et al., "A convenient Dealkylation of Dialkyl Phosphonates by Chlorotrimethylsilane in the Presence of Sodium Iodide", Tetrahedron Letters No. 28, pp. 2523-2526, 1978.
Vogtle, et al., "Quadratsaure und Oxalsaure als Bausteine neuer Kronenetheramine und Cryptanden", Liebigs Ann. Chem. (1977) pp. 1698-1706.
Tietze et al., "Squaric acid diethyl ester: a new coupling reagent for the formation of drug biopolymer conjugates. Synthesis of squaric acid ester amides & diamides" (1991) Inst. Org. Chem. (Abstract only).
Chenard, et al., "A unified approach to systematic isosteric substitutions for acidic groups and application to NMDA antagonists related to 2-amino-7-phosphonoheptanoate.", J Med Chem. Mar. 1990;33(3):1077-83.
23- Allphatics, 1991, 114, 717, Abs. No. 246836q.
Childers et al., "Neuroprotectant Competitive NMDA Antagonist" Drugs of the Future 2002, 27(7):633-638.
Kinney et al., "Design and synthesis of [2-(8,9-dioxo-2,6-diazabicyclo[5.2.0]non-1(7)-en-2-yl)-ethyl]phosphonic acid (EAA-090), a potent N-methyl-D-aspartate antagonist, via the use of 3-cyclobutene-1,2-dione as an achiral alpha-amino acid bioisostere." J Med Chem. Jan. 15, 1998;41(2):236-46.

(Continued)

*Primary Examiner*—Brenda Coleman
(74) *Attorney, Agent, or Firm*—Michael P. Straher; Joel Silver; Barbara Renda

(57) ABSTRACT

The present invention provides methods for the preparation of {2-[(8,9)-dioxo-2,6-diaza-bicyclo[5.2.0]-non-1(7)-en-2-yl]ethyl}phosphonic acid, and esters thereof.

28 Claims, No Drawings

OTHER PUBLICATIONS

Kinney et al., "Bioisosteric replacement of the alpha-amino carboxylic acid functionality in 2-amino-5-phophonopentanoic acid yields unique 3,4-diamino-3-cyclobutene-1,2-dione containing NMDA antagonists." J Med Chem. Dec. 11, 1992;35(25):4720-6.

Baudy et al., "Design, synthesis, SAR, and biological evaluation of highly potent benzimidazole-spaced phosphono-alpha-amino acid competitive NMDA antagonists of the AP-6 type." J Med Chem. May 10, 2001;44(10):1516-29.

Baudy et al. "Potent quinoxaline-spaced phosphono alpha-amino acids of the AP-6 type as competitive NMDA antagonists: synthesis and biological evaluation." J Med Chem. Feb. 5, 1993;36(3):331-42.

Swahn et al., "New Heteroacyl-Spaced phosphono a-amino acids are competitive NMDA antagonists with analgesic activity", Bioorganic & Medicinal Chemistry Letters, 1996: pp. 1635-1640.

Schmutz et al., "Selfotel (CGS19755)" reference in 1997 Academic Press publication on Excitatory Amino Acids—Clinical Results With Antagonists edited by P.L. Herrling.

Boyd, et al. "Reaction of dehydrodithizone with tetraphenylcyclopentadienone. X-Ray crystal structures of a stable 1,5-dipole, azobenzene $N$-($cis$-3a,6a-dihydro-4-oxo-3a,5,6,6a-tetraphenyl-4$H$-cyclopentathiazol-2-yl)-imide, and of $cis$-3a,6a-dihydro-3a,5,6,6a-tetraphenyl-2-phenylazo-4$H$-cyclopentathiazol-4-one" J.C.S. Perkin (1977) pp. 965-971.

Olah, et al., "Iodotrimethylsilane-A Versatile Synthetic Reagent" (1982) Tetrahedron vol. 38;2225-2277.

Derwent World Patent Index record for DE 1518660, 1969.

Abou-Gharbia, Magid, "Optimization of natural procedures leads: discovery of Mylotarg, CCI-779 and GAR-936", Biodiversity, (Proc. IUPAC Int. Conf.), 3rd, 2002, , Abstract.

METHODS FOR THE PREPARATION OF {2-[(8,9)-DIOXO-2,6-DIAZA-BICYCLO[5.2.0]-NON-1(7)-EN-2-YL]ETHYL}PHOSPHONIC ACID AND ESTERS THEREOF

CROSS REFERENCE TO RELATED APPLICATIONS

This application claims the priority benefit of U.S. Provisional Application Ser. No. 60/513,611, filed on Oct. 22, 2003, the disclosure of which is incorporated herein by reference in its entirety.

FIELD OF THE INVENTION

The present invention relates to methods for the preparation of {2-[(8,9)-dioxo-2,6-diaza-bicyclo[5.2.0]-non-1 (7)-en-2-yl]ethyl}phosphonic acid and esters thereof.

BACKGROUND OF THE INVENTION

Excitatory amino acids such as glutamic acid have been shown to be important neurotransmitters (Johnson, R. L.; Koerner, J. F., *J. Med. Chem.* 1988, 31, 2057), which in excess participate in the sequence of events leading to neuronal damage after cerebral ischemia (Choi, E. W., *Trends Neurosci.* 1988, 11, 465). One important sub-type of excitatory amino acid receptor is the NMDA-receptor, which is defined by the selective agonist N-methyl-D-aspartic acid (NMDA). Blocking the action of endogenous agonist by the selective NMDA-receptor antagonist 4-(3-phosphonopropyl-2-piperazinecarboxylic acid (CPP) has been shown to prevent ischemic brain damage in gerbils (Boast, C. A. et al., *Brain Research*, 1988, 442, 345). Also, NMDA-induced convulsions have been prevented by CPP in mice (Lehmann, J. et al., *J. Pharmacol. Exp. Ther.* 1987, 240, 737). Finally, competitive NMDA antagonists such as CPP have been shown to prevent the Parkinsonian-like symptoms induced by MPTP (1-methyl-4-phenyl-1,2,3,6-tetrahydropyridine) in rats (Turski, L. et al., *Nature* 1991, 349, 414). For these reasons, NMDA-receptor antagonists are considered appropriate for treatment of epilepsy, stroke (Engelsen, B., *Acta Neurol Scand.* 1986, 74, 337), and neurodegenerative disorders such as Alzheimer's disease (Maragos, W. F. et al., *Trends Neurosci.* 1987, 10, 65) and Parkinson's disease. More recently, certain NMDA receptor antagonists have been used for the treatment of pain.

Chemical entities known to be competitive NMDA-receptor antagonists contain the α-amino-carboxylic acid and phosphonic acid functionalities separated by a variety of spacer units. An unembellished example is 2-amino-5-phosphonovaleric acid (AP5) (Watkins, J. C.; Evans, R. H., *Annu. Rev. Pharmacol. Toxicol.* 1981, 21, 165), which contains a saturated carbon chain. More complex examples, which contain elements enhancing structural rigidity and therefore potency, include CPP (see above), cis-4-(phosphonomethyl)-2-piperidinecarboxylic acid (CGS-19755) (Lehman, J. et al., *J. Pharmacol. Exp. Ther.* 1988, 246, 65), and (E)-2-amino-4-methyl-5-phosphono-3-pentenoic acid (CGP-37849) (Schmutz, M. et al., *Abs. Soc. Neurosci.* 1988, 14, 864). The compound of {2-[(8,9)-dioxo-2,6-diaza-bicyclo[5.2.0]-non-1 (7)-en-2-yl]ethyl}phosphonic acid is a NMDA antagonist which, inter alia, prevents NMDA-induced lethality in vivo, and is useful as anticonvulsants and neuroprotectants in situations involving excessive release of excitatory amino acids. See U.S. Pat. No. 5,168,103, incorporated herein by reference in its entirety.

Given the importance of NMDA antagonist, it is clear that improved synthetic routes to {2-[(8,9)-dioxo-2,6-diaza-bicyclo[5.2.0]-non-1 (7)-en-2-yl]ethyl}phosphonic acid are needed. This invention is directed to this, as well as other, important ends.

SUMMARY OF THE INVENTION

The present invention provides methods for preparing {2-[(8,9)-dioxo-2,6-diaza-bicyclo[5.2.0]-non-1(7)-en-2-yl]ethyl}phosphonic acid, which has the Formula I:

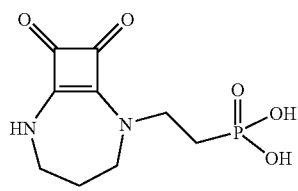

and esters thereof having the Formula IV:

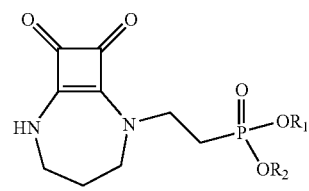

wherein $R_1$ and $R_2$ are independently $C_{1-6}$ alkyl or $C_{1-6}$ haloalkyl.

In some embodiments, the methods comprise reacting, in a solvent, a compound of Formula II:

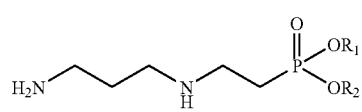

with a compound of Formula III:

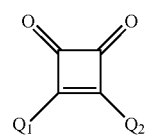

wherein:
  $Q_1$ and $Q_2$ are each independently OH, halogen, or $OX_1$, where $X_1$ is $C_{1-6}$ alkyl, $C_{1-6}$ haloalkyl or aryl; and said solvent has the formula $HOX_1$;
  for a time and under conditions effective to produce said compound of Formula IV.

In some preferred embodiments, $Q_1$ and $Q_2$ are identical. In some embodiments, when $Q_1$ and $Q_2$ have the formula $OX_1$, then the $X_1$ moiety of the solvent is not the same as the $X_1$ moiety of $Q_1$ and $Q_2$.

In some embodiments, the methods further comprise the step of hydrolyzing said compound of Formula IV to provide the compound of Formula I:

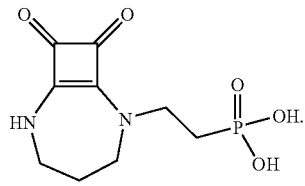

I

In some embodiments, the compound of Formula II is prepared by reacting a compound of Formula V or Formula VI:

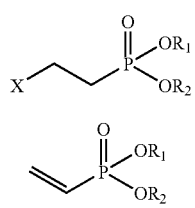

V

VI wherein X is a leaving group, with 1,3-diaminopropane.

In some embodiments of the disclosed methods, $R_1$ and $R_2$ are each independently methyl, ethyl, propyl (e.g., n-propyl or isopropyl), or butyl (e.g., n-butyl, t-butyl). In some embodiments of the disclosed methods, $R_1$ and $R_2$ are each ethyl. In further embodiments, $R_1$ and $R_2$ are the same. In some further embodiments, the solvent is methanol or ethanol. In some embodiments, the solvent is methanol.

In some embodiments, $Q_1$ and $Q_2$ are each OH. In further embodiments, $Q_1$ and $Q_2$ are each halogen. In still further embodiments, $Q_1$ and $Q_2$ are each $OX_1$ wherein $X_1$ is $C_{1-6}$ alkyl, preferably methyl, ethyl, n-propyl, isopropyl, n-butyl, or t-butyl.

In some preferred embodiments, $Q_1$ and $Q_2$ are each $OCH_2CH_3$. In further preferred embodiments, $Q_1$ and $Q_2$ are each $OCH_2CH_3$, and the solvent is methanol.

In some further preferred embodiments of the methods, $Q_1$ and $Q_2$ are each OH, and the solvent is methanol.

In some further embodiments, each $Q_1$ and $Q_2$ are each $OX_1$ wherein $X_1$ is haloalkyl. In still further embodiments, each $Q_1$ and $Q_2$ are each $OX_1$ wherein $X_1$ is aryl.

In some embodiments, $Q_1$ and $Q_2$ are the same, and in other embodiments, $Q_1$ and $Q_2$ are different.

In some embodiments, $Q_1$ and $Q_2$ are each $OX_1$; wherein each $X_1$ is the same. In some further embodiments, $R_1$ and $R_2$ are each independently methyl, ethyl, propyl, or butyl; each of said $Q_1$ and $Q_2$ is $OX_1$ wherein $X_1$ is independently methyl, ethyl, n-propyl, isopropyl, n-butyl or t-butyl; and said solvent is methanol or ethanol. In still further embodiments, $R_1$ and $R_2$ are each independently methyl or ethyl; each of said $Q_1$ and $Q_2$ is $OX_1$ wherein $X_1$ is ethyl, and said solvent is methanol. In still further embodiments, $R_1$ and $R_2$ are each independently methyl or ethyl; each of said $Q_1$ and $Q_2$ is OH; and said solvent is methanol or ethanol.

In some further embodiments, $R_1$ and $R_2$ are each independently methyl or ethyl; each of said $Q_1$ and $Q_2$ is halogen, preferably chlorine, and said solvent is methanol or ethanol.

In some embodiments, X is halo.

In further embodiments, X is Cl or Br.

In some embodiments, the molar ratio of said 1,3-diaminopropane to said compound of Formula V or Formula VI is at least about 2:1, preferably at least about 3:1, more preferably at least about 4:1, and more preferably at least about 5:1.

In some embodiments, the reaction of compounds of Formulas II and III is performed at a temperature of from about 10° C. to a temperature below the solvent boiling point, about 50° C. to about 70° C., preferably a temperature of from about 55° C. to about 65° C., more preferably at a temperature of about 60° C.

In some embodiments wherein the compound of Formula II is prepared by reacting 1,3-diaminopropane with the compound of Formula V, the compound of Formula II is collected in a yield of greater than about 50%, preferably in a yield of greater than about 60%.

In some embodiments, the reaction of said compound of Formula V and 1,3-diaminopropane is performed at a temperature of from about 10° C. to about 50° C., preferably from about 10° C. to about 40° C., more preferably from about 15° C. to about 35° C., more preferably from about 20° C. to about 30° C.

In some embodiments wherein the compound of Formula II is prepared by reacting 1,3-diaminopropane with a compound of Formula VI, the compound of Formula II is collected in a yield of greater than about 95%, preferably greater than about 98%.

In some embodiments, the reaction of the compound of Formula VI and 1,3-diaminopropane is performed at a temperature of from about 10° C. to about 60° C., preferably from about 15° C. to about 50° C., more preferably from about 15° C. to about 45° C., and more preferably from about 20° C. to about 40° C.

In some embodiments of each of the foregoing methods, compound of Formula II and the compound of Formula III are reacted in substantially equimolar amounts.

The present invention further provides a product made by the process of:

a) reacting, in a solvent, a compound of Formula II:

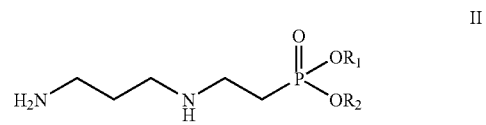

II wherein $R_1$ and $R_2$ are independently $C_{1-6}$ alkyl or $C_{1-6}$ haloalkyl; with a compound of Formula III:

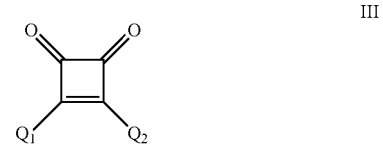

III wherein $Q_1$ and $Q_2$ are each independently OH, halogen, or $OX_1$, wherein $X_1$ is $C_{1-6}$ alkyl, $C_{1-6}$ haloalkyl or aryl; and said solvent has the formula $HOX_1$; for a time and under conditions effective to produce a compound of Formula IV:

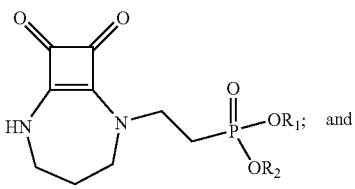

and b) hydrolyzing said compound of Formula IV to provide a compound of Formula I:

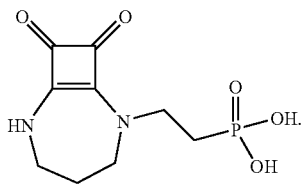

In some embodiments, the above product comprises at least one compound selected from Formulas VII, VIII, IX, or X and any combination thereof:

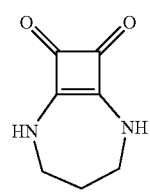

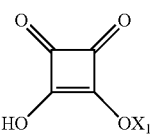

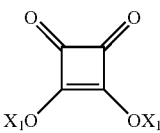

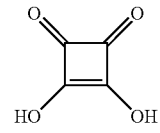

wherein $X_1$ is $C_{1-6}$ alkyl, $C_{1-6}$ haloalkyl or aryl. In preferred embodiments, the product comprises at least one compound selected from Formulas VII, VIII, IX or X. In a preferred embodiment, the product contains the compound of Formula IX in an amount less than about 0.1%, less than about 0.05%, or less than about 0.01% by weight.

The present invention further provides compositions comprising a compound of Formula IV:

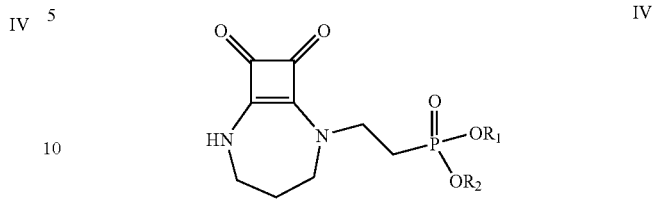

wherein $R_1$ and $R_2$ are each independently $C_{1-6}$ alkyl or $C_{1-6}$ haloalkyl; and at least one compound selected from Formulas VII, VIII, IX, and X; wherein $X_1$ is $C_{1-6}$ alkyl, $C_{1-6}$ haloalkyl or aryl. In some embodiments, $X_1$ is ethyl. In some embodiments, $R_1$ and $R_2$ are both ethyl.

In some embodiments, the present invention provides a composition comprising a compound of Formula I and at least one compound selected from. Formulas VII, VIII, IX, and X, wherein $X_1$ is $C_{1-6}$ alkyl, $C_{1-6}$ haloalkyl or aryl. In some embodiments, at least one compound selected from Formulas VII, VIII, IX, and X is present in said composition containing the compound of Formula I in an amount less than about 50% by weight. In further embodiments the composition comprises a compound of Formula VII or X. In yet further embodiments, the composition comprises a compound of Formula VII.

DETAILED DESCRIPTION

The present invention provides, inter alia, methods for preparing {2-[(8,9)-dioxo-2,6-diaza-bicyclo[5.2.0]-non-1(7)-en-2-yl]ethyl}phosphonic acid, and esters thereof. The methods disclosed herein allow for the preparation of the subject compounds without the use of N-protected 1,3-diaminocyclopropane, and without the use of a reducing agent.

In some embodiments, the methods comprise reacting, in a solvent, a compound of Formula II:

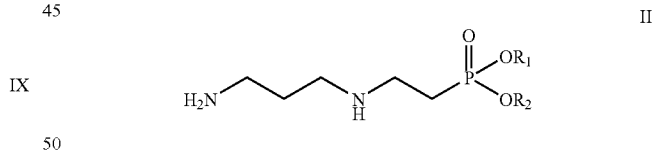

with a compound of Formula III:

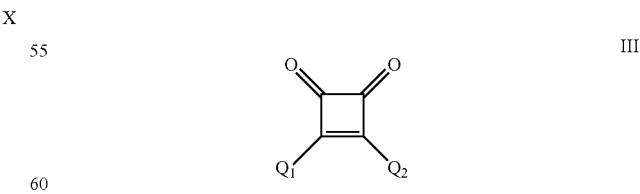

wherein:

$R_1$ and $R_2$ are independently $C_{1-6}$ alkyl or $C_{1-6}$ haloalkyl;

$Q_1$ and $Q_2$ are each independently OH, halogen, or $OX_1$, where $X_1$ is $C_{1-6}$ alkyl, $C_{1-6}$ haloalkyl or aryl; and the solvent has the formula $HOX_1$;

for a time and under conditions effective to produce a compound of Formula IV:

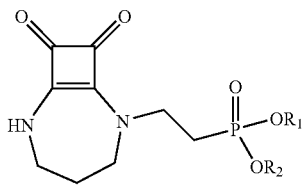

In some preferred embodiments of the invention, the squarate substituents $Q_1$ and $Q_2$ are identical. In further embodiments, when $Q_1$ and $Q_2$ have the formula $OX_1$, the $X_1$ moiety of the solvent is preferably not the same as the $X_1$ moiety of $Q_1$ and $Q_2$.

In some embodiments, $R_1$ and $R_2$ are each, independently, methyl, ethyl, propyl (e.g., n-propyl, isopropyl), or butyl (e.g., n-butyl, t-butyl). In some embodiments, $R_1$ and $R_2$ are each, independently, methyl or ethyl. In some embodiments, $R_1$ and $R_2$ are each, ethyl.

The reaction of the N-(3-aminopropyl)aminoethanephosphonic acid ester of Formula II with the squaric acid or squarate derivative thereof of Formula III can be performed using a wide variety of solvents. In some preferred embodiments, alcohol solvents are generally preferred, particularly those having the Formula $HOX_1$ as described above. Non-limiting examples of preferred solvents include methanol, ethanol, isopropanol and butanol. In some embodiments, the weight ratio of solvent to compound of Formula III is about 10 to about 500, 50 to about 500, about 100 to about 300, about 150 to about 250, about 175 to about 225, or about 200.

It is generally preferred to perform the reaction of compounds of Formulas II and III using substantially equimolar amounts of each compound (i.e., having no more than about 5% molar excess of one of the compound in the reaction mixture), thus providing the benefit of using smaller quantities of starting materials. It is also generally preferred to carry out the reaction of compounds of Formulas II and III using dilute reaction conditions. In some embodiments, the reaction is carried out where the ratio of reagent (amount of compounds of Formulas II and III in grams) to total solvent (mL) is from about 1:50 to about 1:1000, about 1:100 to about 1:500, about 1:120 to about 1:200, or about 1:140.

While not wishing to be bound by any particular theory, it is believed that the present methods minimize undesired reactions by taking advantage of both the greater reactivity of the primary amino group of the N-(3-aminopropyl)aminoethanephosphonic acid ester, and, in some embodiments, by using an alcohol solvent that will lead to the formation of mixed squarate esters that have centers of differing reactivity. The use of a solvent suitable for such exchange with squarate $Q_1$ and/or $Q_2$ groups can provide the additional benefit of affording the use of a variety of squarate ester compounds of Formula III, and forming the reactive species in situ through exchange of $Q_1$ or $Q_2$ groups with solvent. Thus, squarate ester compounds of Formula III can have a variety of groups at positions $Q_1$ and $Q_2$, including halogens and oxygen leaving groups such as alkoxy, haloalkoxy, and aryloxy moieties. In some preferred embodiments, the leaving group $Q_1/Q_2$ is lower alkoxy, particularly ethoxy, isopropoxy or butoxy.

The reaction of compounds of Formulas II and III can be performed at a temperature of from about 10° C. to a temperature below the solvent boiling point, from about 50° C. to about 70° C., preferably a temperature of from about 55° C. to about 65° C., more preferably at a temperature of about 60° C.

In some embodiments, the reaction of compounds of Formulas II and III can be performed by simultaneously adding solutions of the two compounds in the solvent of Formula $HOX_1$ to a vessel containing preheated solvent. The product of the reaction can be collected in good yield and purity from the reaction mixture by any suitable technique, for example by recrystallization from a suitable solvent, for example ethyl acetate.

In some embodiments, the compound of Formula II is prepared by reacting a phosphonate of Formula V, or a vinyl phosphonate of Formula VI:

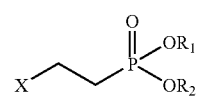

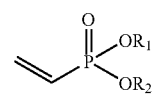

wherein X is a leaving group, with 1,3-diaminopropane. In such embodiments, it is beneficial to employ an excess of 1,3-diaminopropane to minimize formation of the disubstituted diamine. Thus, in preferred embodiments, the molar ratio of 1,3-diaminopropane to the compound of Formula V or Formula VI is at least about 2:1, preferably at least about 3:1, more preferably at least about 4:1, and more preferably at least about 5:1.

The reaction of the compounds of Formula V or VI with 1,3-diaminopropane can be conveniently performed at a wide range of temperatures; e.g. from about 10° C. to about 60° C. or higher. In some embodiments, the reaction of the compound of Formula V and 1,3-diaminopropane can be performed at a temperature of from about 10° C. to about 50° C., preferably from about 10° C. to about 40° C., more preferably from about 15° C. to about 35° C., more preferably from about 20° C. to about 30° C. In some other embodiments, the reaction of the compound of Formula VI and 1,3-diaminopropane is performed at a temperature of from about 10° C. to about 60° C., preferably from about 15° C. to about 50° C., more preferably from about 15° C. to about 45° C., and more preferably from about 20° C. to about 40° C.

In some preferred embodiments, the reaction of the compound of Formula V or VI and 1,3-diaminopropane is performed by adding the compound of Formula V or VI to a solution of 1,3-diaminopropane in a solvent that is preferably, but not limited to, an alcohol solvent. Suitable solvents include those having the Formula $HOX_1$ as described herein. Preferred solvents include lower alcohols, for example methanol, ethanol, isopropanol and butanol, with methanol being most preferred. In some embodiments, the weight ratio (e.g., g/g) of solvent to 1,3-diaminopropane is about 10 to about 500, about 20 to about 300, about 30 to about 200, or about 40 to about 125. The product of the reaction can be purified by any suitable technique, for example by silica gel chromatography.

According to further aspects of the invention, one or more compounds of Formulas VII, VIII, IX, or X or any combination thereof:

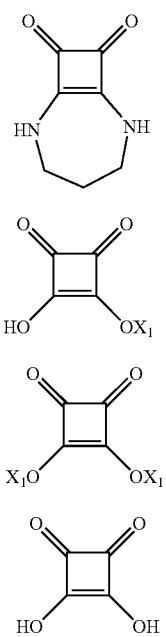

can be formed as byproducts in the above described reactions. The byproducts can be detected and quantified by routine methods such as by HPLC or LCMS. In some embodiments, the present invention includes compositions comprising a compound of Formula IV or I and at least one byproduct of Formula VII, VIII, IX, or X. In some embodiments, $X_1$ is ethyl. In further embodiments, the byproduct of Formula VII, VIII, IX, or X is present in a composition as a minor component (e.g., less than about 50% by weight). In some embodiments, the byproduct is present in a composition in an amount less than about 40%, less than about 30%, less than about 20%, less than about 20%, less than about 10% less than about 5%, less than about 2%, less than about 1%, less than about 0.5%, less than about 0.1%, less than about 0.05% or less than about 0.01% by weight based on the total weight of the composition. In a preferred embodiment, when $HOX_1$ is methanol, the compound of Formula IX is present in an amount less than about 0.1%, preferably less than about 0.05%, or more preferably less than about 0.01% in the composition containing Formula I or IV. In other embodiments, when $HOX_1$ is ethanol the product preferably does contain a compound of Formula IX in the composition containing Formula I or IV.

In some embodiments, squarate byproducts of Formula VII or IX which are present in compositions containing bicyclic phosphate ester compounds of Formula IV can be hydrolyzed to form squaric acid of Formula X under reaction conditions suitable for hydrolysis of the compound of phosphate ester compounds of Formula IV to form the phosphate of Formula I. Accordingly, the present invention includes compositions containing a compound of Formula I and a compound of Formula VII or X. In some embodiments, the amount of compound of Formula VII or X in a composition containing Formula I is less than about 50%, less than about 40%, less than about 30%, less than about 20%, less than about 10%, less than about 5%, less than about 2%, less than about 1%, less than about 0.5%, less than about 0.1%, less than about 0.05%, or less than about 0.01% by weight based on the total composition.

As used herein, the term "alkyl" or "alkylene" is meant to refer to a saturated hydrocarbon group which is straight-chained, branched or cyclic. Example alkyl groups include those of 1-6 carbon atoms such as methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. "Haloalkyl" refers to an alkyl group substituted by one or more halogen atoms. Example haloalkyl groups include $CHF_2$ and $CF_3$.

As used herein, "alkenyl" refers to an alkyl group having one or more double carbon-carbon bonds. Example alkenyl groups include those of 2-6 carbon atoms such as ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include those having 2-6 carbon atoms such as ethynyl, propynyl, butynyl, pentynyl, and the like.

As used herein, "halo" or "halogen" refers to fluoro, chloro, bromo, and iodo.

As used herein, "alkoxy" refers to an —O-alkyl group. Example alkoxy groups include those having 1-6 carbon atoms such as methoxy, ethoxy, propoxy (e.g., n-propoxy and isopropoxy), t-butoxy, and the like.

As used herein, "aryl" refers to monocyclic or polycyclic aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, the term "reacting" refers to the bringing together of designated chemical reactants such that a chemical transformation takes place generating a compound different from any initially introduced into the system.

As used herein, the term "leaving group" refers to a moiety that can be selectively displaced by another moiety, such as by nucleophilic substitution or elimination, during a chemical reaction. Typically, leaving groups include moieties that when removed by nucleophilic substitution or elimination are relatively stable in anionic form. Leaving groups are well known in the art and include, for example, halides (e.g., chloride, bromide, and iodide) and alkyl- and arylsulfonates such as mesylate, tosylate, brosylate, nosylate, triflate, and the like.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, $C_6$ alkyl.

Where compounds of the present methods can contain one or more asymmetric atoms, and thus give rise to optical isomers (enantiomers) and diastereomers, methods of the present invention include all such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The methods described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The reactions of the processes described herein are preferably carried out under an inert atmosphere, for example nitrogen or a noble gas.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLE 1

Preparation of N-(3-aminopropyl)aminoethanephosphonic acid diethyl ester via N-alkylation of 1,3-diaminopropane

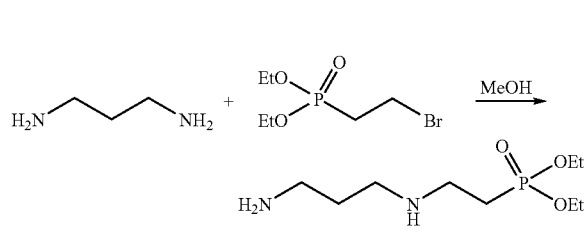

To a 100-mL three-necked flask equipped with a magnetic stirrer and a nitrogen inlet, methanol (50 mL) was added followed by 1,3-diaminopropane (3.38 g, 46 mmol, 5.0 equiv). The reaction was exothermic (21.0 to 30.2° C.). It was stirred for 10 min. then diethyl (2-bromoethyl)phosphonate (DBEP) (2.24 g) was added. The mixture was stirred overnight (HPLC-monitored disappearance of DBEP, 0.66%) and then it was transferred to a 500-mL flask, silica gel (5.0 g) was added and the mixture was concentrated on a rotovap. The sample was loaded on a short column (30.0 g of silica gel), eluted with dicholoromethane/methanol (9/1 containing 1% $Et_3N$) to remove 1,3-diaminopropane and the dialkylated product, then eluted with dichlormethane/methanol (1/1, containing 1% $Et_3N$) to obtain the desired product as a colorless oil (1.33 g, 61% yield relative to DBEP, purity 97.6% HPLC area).

EXAMPLE 2

Preparation of N-(3-aminopropyl)aminoethanephosphonic acid diethyl ester via addition of 1,3-diaminopropane to diethyl vinylphosphonate

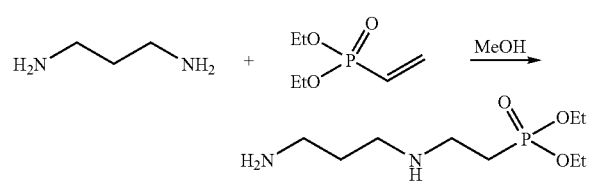

To a 500-mL, three-necked flask, equipped with a magnetic stirrer and a nitrogen inlet, methanol (150 mL) and 1,3-diaminopropane (12.7 g, 152 mmol, 5.0 equiv) were added (exothermic, 21.0 to 40.2° C.). The reaction mixture was stirred for 10 min. then diethyl vinylphosphonate (DEVP) (5.0 g) was added. The mixture was stirred overnight, transferred to a 500-mL flask and methanol was removed. The residue was loaded on a short column (50.0 g of silica gel) and eluted with 1000 mL or dichloromethane (containing 1% $Et_3N$) and 1000 mL of dichloromethane/methanol (1/1, 1% $Et_3N$). Evaporation of the solvents gave the desired product as colorless oil (7.08 g, 98% yield relative to DEVP, purity 88% HPLC area).

EXAMPLE 3

Preparation of 2-[(8,9)-dioxo-2,6-diaza-bicyclo[5.2.0]-non-1(7)-en-yl]ethyl}phosphonic acid diethyl ester

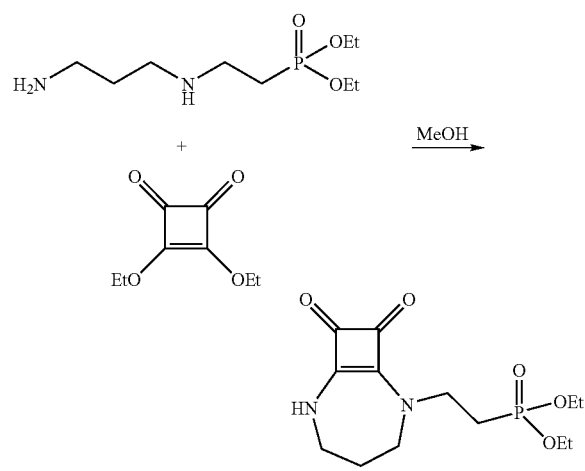

To a 500-mL, three-necked flask, equipped with a magnetic stirrer and a nitrogen inlet, methanol (250 mL) was added and the content was heated to 60° C. Diethyl squarate (1.04 g) was dissolved in methanol (50 mL) and the solution transferred to a syringe. Similarly, N-(3-aminopropyl)-2-aminoethane phosphonic acid diethyl ester (1.46 g) was dissolved in methanol (50 mL) and transferred to a syringe. The two solutions were concomitantly added via a syringe pump into preheated methanol over six hours. The mixture was stirred overnight at room temperature, most of methanol was evaporated and ethyl acetate (50 mL) was added to the residue. After cooling in an ice bath, the product was filtered (1.05 g, 54% yield relative to N-(3-aminopropyl)-2-amino-ethane phosphonic acid diethyl ester).

In a reaction conducted substantially according to the above protocol, the crude product contained, in addition to the title compound, a squarate compound having formula:

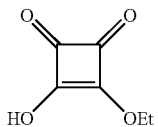

as a minor component (14.63% peak area by LC/MS).

In a reaction conducted substantially according to the above protocol, except where methanol solvent was replaced with ethanol, the crude product contained, in addition to the title compound, a squarate compound having formula:

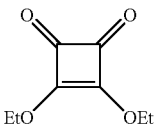

as a minor component (16.62% peak area by LC/MS).

In a reaction conducted substantially according to the above protocol, the crude product contained, in addition to the title compound, a bicyclic compound having formula:

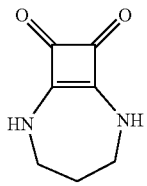

as a minor component (27.74% peak area by LC/MS).

EXAMPLE 4

2-[(8,9)-dioxo-2,6-diaza-bicyclo[5.2.0]-non-1(7)-en-yl]ethyl}phosphonic acid

Hydrolysis of 2-[(8,9)-dioxo-2,6-diaza-bicyclo[5.2.0]-non-1(7)-en-yl]ethyl}phosphonic acid diethyl ester from Example 3 to yield 2-[(8,9)-dioxo-2,6-diaza-bicyclo[5.2.0]-non-1(7)-en-yl]ethyl}phosphonic acid is accomplished by reaction with bromotrimethylsilane according to the procedure disclosed in Example 8 of U.S. Pat. No. 5,168,103, or by reaction with chlorotrimethylsilane/NaI/methanol according to the procedure of *Tetrahedron Lett.*, 1978, 28, 2523.

As those skilled in the art will appreciate, numerous changes and modifications may be made to the preferred embodiments of the invention without departing from the spirit of the invention. It is intended that all such variations fall within the scope of the invention.

It is intended that each of the patents, applications, and printed publications including books mentioned in this patent document be hereby incorporated by reference in their entirety.

What is claimed is:

1. A method for preparing a compound of Formula IV:

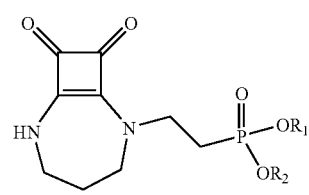

wherein $R_1$ and $R_2$ are independently $C_{1-6}$ alkyl or $C_{1-6}$ haloalkyl;

comprising the step of reacting, in a solvent, a compound of Formula II:

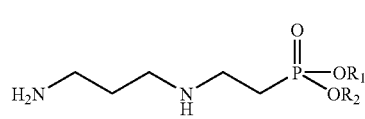

with a compound of Formula III:

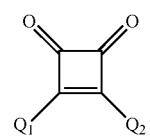

wherein:
  $Q_1$ and $Q_2$ are each independently OH, halogen, or $OX_1$, where $X_1$ is $C_{1-6}$ haloalkyl or aryl; and said solvent is methanol, ethanol, or has the formula $HOX_1$;
to produce said compound of Formula IV.

2. The method of claim 1 further comprising the step of hydrolyzing said compound of Formula IV to provide a compound of Formula I:

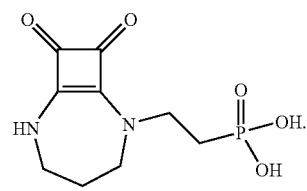

3. A method for preparing a compound of Formula IV:

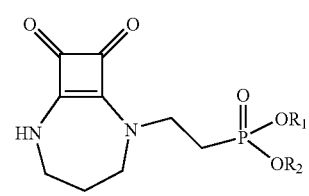

wherein $R_1$ and $R_2$ are independently $C_{1-6}$ alkyl or $C_{1-6}$ haloalkyl;

comprising the step of reacting a compound of Formula V or Formula VI:

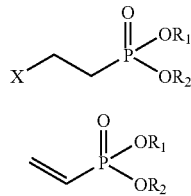

wherein X is a leaving group, with 1,3-diaminopropane to produce a compound of Formula II;
reacting, in a solvent, a compound of Formula II:

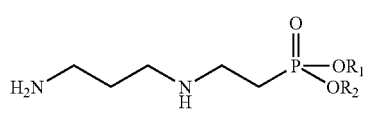

with a compound of Formula III:

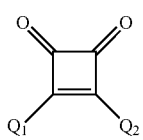

wherein:
 $Q_1$ and $Q_2$ are each independently OH, halogen, or $OX_1$, where $X_1$ is $C_{1-6}$ alkyl, $C_{1-6}$ haloalkyl or aryl; and said solvent has the formula $HOX_1$;
to produce said compound of Formula IV.

4. The method of claim 1 or 3 wherein $R_1$ and $R_2$ are each independently methyl, ethyl, propyl, or butyl.

5. The method of claim 1 or 3 wherein $R_1$ and $R_2$ are each ethyl.

6. The method of claim 1 or 3 wherein $R_1$ and $R_2$ are the same.

7. The method of claim 3 wherein said solvent is methanol or ethanol.

8. The method of claim 1 or 3 wherein $Q_1$ and $Q_2$ are each OH.

9. The method of claim 1 or 3 wherein $Q_1$ and $Q_2$ are each halogen.

10. The method of claim 3 wherein $Q_1$ and $Q_2$ are each $OX_1$ wherein $X_1$ is $C_{1-6}$ alkyl.

11. The method of claim 3 wherein $Q_1$ and $Q_2$ are each $OX_1$ wherein $X_1$ is methyl, ethyl, isopropyl or n-butyl.

12. The method of claim 10 wherein $Q_1$ and $Q_2$ are the same.

13. The method of claim 3 wherein $Q_1$ and $Q_2$ are each $OCH_2CH_3$.

14. The method of claim 3 wherein $Q_1$ and $Q_2$ are each $OCH_2CH_3$, and said solvent is methanol.

15. The method of claim 1 wherein $Q_1$ and $Q_2$ are each OH, and said solvent is methanol.

16. The method of claim 1 or 3 wherein each $Q_1$ and $Q_2$ are each $OX_1$ wherein $X_1$ is haloalkyl.

17. The method of claim 1 or 3 wherein $Q_1$ and $Q_2$ are each $OX_1$ wherein $X_1$ is aryl.

18. The method of claim 3 wherein $R_1$ and $R_2$ are each independently methyl or ethyl; each of said $Q_1$ and $Q_2$ is $OX_1$ wherein $X_1$ is independently methyl, ethyl, isopropyl or n-butyl; and said solvent is methanol or ethanol.

19. The method of claim 3 wherein the molar ratio of said 1,3-diaminopropane to said compound of Formula V or Formula VI is at least about 2:1.

20. The method of claim 3 wherein X is halo.

21. The method of claim 3 wherein said compound of Formula II is prepared by reacting 1,3-diaminopropane with said compound of Formula V.

22. The method of claim 3 wherein compound of Formula II is prepared by reacting 1,3-diaminopropane with a compound of Formula VI.

23. The method of claim 1 or 3 wherein said compound of Formula II and said compound of Formula III are reacted in substantially equimolar amounts.

24. A product made by the process comprising:
a) reacting, in a solvent, a compound of Formula II:

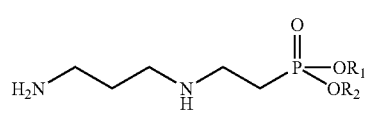

wherein $R_1$ and $R_2$ are independently $C_{1-6}$ alkyl or $C_{1-6}$ haloalkyl;
with a compound of Formula III:

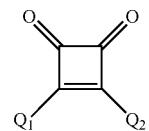

wherein $Q_1$ and $Q_2$ are each independently OH, halogen, or $OX_1$, wherein $X_1$, is $C_{1-6}$ alkyl, $C_{1-6}$ haloalkyl or aryl; and
said solvent has the formula $HOX_1$;
to produce a compound of Formula IV:

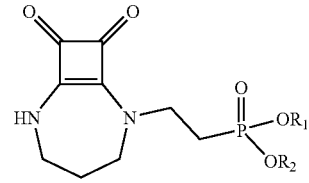

b) hydrolyzing said compound of Formula IV to provide a compound of Formula I:

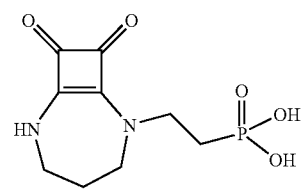

said product further comprising at least one compound selected from Formulas VII, VIII, IX, and X:

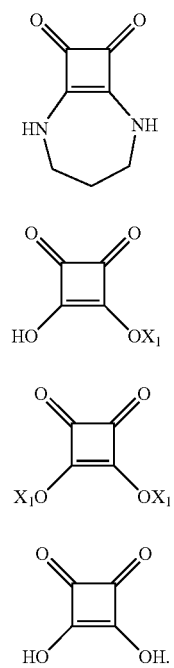

25. A composition comprising a compound of Formula IV:

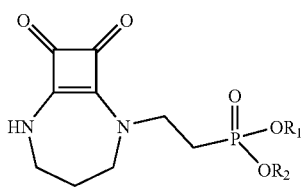

wherein $R_1$ and $R_2$ are independently $C_{1-6}$ alkyl or $C_{1-6}$ haloalkyl; and at least one compound selected from Formulas VII, VIII, IX, and X:

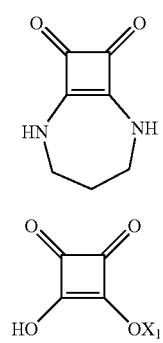

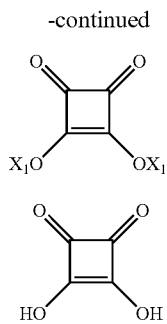

wherein $X_1$ is $C_{1-6}$ alkyl, $C_{1-6}$ haloalkyl or aryl.

26. The composition of claim 25 wherein $X_1$ is ethyl.

27. The composition of claim 25 wherein $R_1$ and $R_2$ are ethyl.

28. A composition comprising a compound of Formula I:

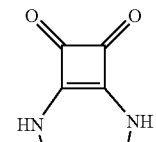

and at least one compound selected from Formulas VII, VIII, IX, and X:

wherein $X_1$ is $C_{1-6}$ alkyl, $C_{1-6}$ haloalkyl or aryl.

* * * * *